United States Patent [19]

Kraus et al.

[11] Patent Number: 4,965,267

[45] Date of Patent: Oct. 23, 1990

[54] PYRANOQUINONES WITH ANTICOCCIDIAL ACTIVITY

[75] Inventors: George A. Kraus; Donald L. Reynolds, both of Ames, Iowa

[73] Assignee: Iowa State University Research Foundation, Inc., Ames, Iowa

[21] Appl. No.: 395,992

[22] Filed: Aug. 21, 1989

[51] Int. Cl.$^5$ .................... A01N 43/58; C07D 307/77
[52] U.S. Cl. ...................................... 514/253; 549/298
[58] Field of Search ......................... 549/298; 514/453

[56] References Cited

U.S. PATENT DOCUMENTS

| 3,365,456 | 1/1968 | Petrzilka | 549/298 |
|---|---|---|---|
| 3,524,865 | 8/1970 | Hoeksema | 549/298 |
| 3,632,607 | 1/1972 | Meyer | 549/298 |
| 4,199,514 | 4/1980 | Omura et al. | 549/298 |
| 4,237,057 | 12/1980 | Kraus | 549/298 |
| 4,414,226 | 11/1983 | Ikushima et al. | 549/298 |
| 4,530,845 | 7/1985 | Isushima et al. | 514/453 |
| 4,639,467 | 1/1987 | Celino et al. | 514/468 |
| 4,740,521 | 4/1988 | Mossa | 514/453 |

FOREIGN PATENT DOCUMENTS

| 0004128 | 9/1979 | European Pat. Off. | 549/298 |
|---|---|---|---|
| 53-3591 | 1/1978 | Japan | 549/298 |
| 58-88313 | 5/1983 | Japan | 549/298 |
| 59-78112 | 5/1984 | Japan | 549/298 |

OTHER PUBLICATIONS

Tetrahedron Letters, vol. 29, No. 46, pp. 5987-5990 (1988).

*Primary Examiner*—John M. Ford
*Assistant Examiner*—Robert C. Whittenbaugh
*Attorney, Agent, or Firm*—Zarley, McKee, Thomte, Voorhees & Sease

[57] ABSTRACT

A new pyranoquinone and use thereof as an anticoccidial agent.

5 Claims, No Drawings

PYRANOQUINONES WITH ANTICOCCIDIAL ACTIVITY

BACKGROUND OF THE INVENTION

This invention relates to a novel compound particularly useful as an antibiotic substance. It is most useful for treatment of coccidiosis.

Coccidiosis is a known problem for fowl, particularly chickens and turkey. There is therefore a continuing need for development of anticoccidiosis agents.

Two of the most common anticoccidiosis compounds now in use are Coban ® and Salinomycin ®. These compounds while effective have a high degree of toxicity. In particular it is desirable to have an antibiotic which is effective not only as an anticoccidial agent but also has low levels of toxicity in comparison with the anticoccidials currently available, namely Coban and Salinomycin.

The primary objective of the present invention is to fulfill the above-described need for an effective anticoccidial agent which has low toxicity in comparison with those commercially available.

Another objective of the present invention is to provide an improved anticoccidial agent by a simple direct synthesis route which provides a mixture of an enantiomers as opposed to a single enantiomer which might be obtained by fermentation synthesis.

The method and means of accomplishing each of the above objectives will become apparent from the detailed description which follows. The novel compound of the present invention has the formula:

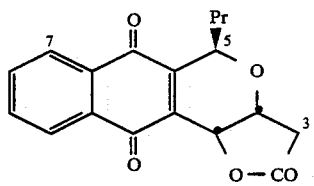

This novel compound has valuable anticoccidial agent properties and in addition provides low levels of toxicity in comparison with presently available commercial anticoccidial agents.

In use in the present invention the compound may be used for treatment of fowl at dosage levels of from 50 parts per million to 150 parts per million, preferably at levels from about 90 parts per million to 110 parts per million. The compound may be added to pre-mix at a weight level sufficient to achieve the weights on a part per million basis as above expressed. It is then homogeneously intermixed with the feed ration and then fed to the animals.

The most closely related known structure of the present compound is frenolicin B as described in U.S. Pat. No. 4,199,514, issued Apr. 22, 1980. Frenolicin B is a different compound having a hydroxyl moiety in position 7 whereas the present claimed compound only has hydrogen in this position. Moreover, the frenolicin B of the description of U.S. Pat. No. 4,199,514 is prepared by a fermentation process by cultivating the microorganism belonging to the genus Streptomyces. Frenolicin B is a single enantiomer prepared by fermentation whereas the compound of the present invention is a mixture of enantiomers prepared by synthesis.

In accordance with the process of the present invention there are essentially three steps. In the first step there is oxidation of a hydroquinone followed by addition of a furan. In the second step, the product of the first step reaction is again oxidized to turn the intermediate phenol product into a second quinone with the lactone ring attached. And in the third and final step of the reaction there is deoxygenation, which removes the hydroxyl group to give the desired pyranoquinone of the present invention. The details of the process are set forth in the descriptive example which follows hereinafter.

Importantly the reaction is a straight forward three-step synthesis, yielding the final product in overall yields, i.e. as much as 48 percent. The reaction does not need unusual conditions. As earlier stated, pressure, etc. do not appear to be critical.

The following examples are offered to further illustrate but not limit the process and product of the present invention.

EXAMPLE 1

To a solution of 2-propionylnaphthydroquinone (2.3 g, 10 mmol) in 100 mL of acetonitrile at room temperature was added ceric ammonium nitrate (12.6 g, 23 mmol) in 10 mL of water. After 10 minutes, the reaction was complete as evidenced by thin layer chromatography. The mixture was poured onto 30 mL of pH 7.2 buffer and the aqueous layer extracted twice with methylene chloride. The organic layer was dried, filtered and concentrated in vacuo. To the crude quinone in 50 mL of dry methylene chloride at $-78°$ C. was added dropwise 2-trimethylsilyloxyfuran (1.87 g, 12 mmol). After 1 hour, removed and the crude product chromatographed on silica gel (3:1 hexanes:ethyl acetate) to afford 1.82 g (58% yield) of keto phenol.

To a slurry of the keto phenol prepared above (1.65 g, 5.29 mmol) in 70 mL of acetonitrile at room temperature was added dropwise a solution of ceric ammonium nitrate (7.2 g, 13.2 mmol) in 7 mL of water. After 15 min, the solution was poured into pH 7.2 buffer (20 mL) and then diluted with 100 mL of water. The reaction was extracted twice with methylene chloride. The organic layer was dried, filtered and concentrated to provide 1.70 g (98% yield) of pure quinone.

To a solution of the quinone prepared above (1.05 g, 3.2 mmol) in 80 mL of methylene chloride at $-78°$ C. was added triethyl silane (1.10 mL, 6.91 mmol) followed by the dropwise addition of boron trifluoride etherate (0.55 mL, 4.5 mmol). The reaction was stirred at $-78°$ C. for 1.5 hours. The solution was diluted with water and methylene chloride and the aqueous layer extracted again with methylene chloride. The organic layer was dried, filtered and concentrated. The crude product was recrystallized from ether to afford 0.85 g (85% yield) of product.

The compound after recrystallization from ether afforded an 85% yield of the pyranoquinone of the present invention and was confirmed to have the molecular structure:

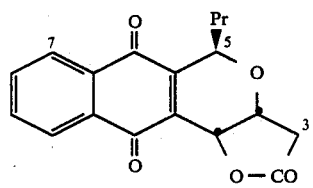

EXAMPLE 2

The compound prepared in example 1 was tested for in vitro toxicity comparison with commercially available anticoccidial agents of Coban and Salinomycin.

In particular, compounds of the present invention were mixed at concentrations set forth in the table below with living cells and then the toxicity to the cells was measured. A toxicity score of 1 indicated slight toxicity with some apparent changes in cells. A minus line indicates no apparent toxicity. A toxicity score of 2 indicates 10% to 50% of the cells affected and a toxicity score of 3 indicates greater than 50% of the cells affected.

TOXICITY DATA FOR COCCIDIOSTATS: IN VITRO ANALYSIS RESULTS

| Concentration of Cmp. (ug/ml) | Invention | Coban (Toxicity Scores)* | Salinomycin |
|---|---|---|---|
| 0 | — | — | — |
| 2.5 | — | — | 1 |
| 5.0 | — | — | 1 |
| 10.0 | — | — | 1 |
| 25.0 | — | — | NT |
| 50.0 | — | — | 3 |
| 100.0 | — | — | NT |
| 150.0 | — | — | NT |
| 200.0 | — | 1 | NT |
| 250.0 | — | 1 | NT |
| 300.0 | — | 1 | NT |
| 350.0 | — | 1 | NT |
| 400.0 | 3 | 1 | NT |
| 450.0 | 3 | 2 | NT |
| 500.0 | 3 | 2 | NT |

*Toxicity scores: 1 - Slight toxicity (apparent changes in some cells) 2 - 10-50% of cells affected 3 - >50% of cells affected NT - Not Tested It can be seen that where the compound of the present invention is used at levels up to 350 micrograms per milliliter the cells showed no visible toxicity whereas toxicity for Coban was observed at a level as low as 50 micrograms per milliliter and for Salinomycin at a level as low as 2.5 micrograms per milliliter. For Salinomycin no testing was done beyond the level of 50 since the highest score of toxicity 3 was already achieved at that level.

When the compound of example 1 is added to feed ration for chickens at a level of 90 parts per million and compared with Coban and Salinomycin at the same level, equal levels of effectiveness from the standpoint of anticoccidial activity are noted.

It can therefore be seen that the invention accomplishes at least all the stated objectives.

EXAMPLE 3

The compound of Example 1 was compared with Coban in an in vitro assay, as set forth in the table below. As can be seen, the compound of the invention appears as effective as Coban ® (5 ug/ml) when it is used at 50 ug/ml. This coupled with the substantially lower and unpredicted toxicity levels of this invention compound demonstrate its usefulness in comparison with Coban ®.

IN VITRO ANICOCCIDIAL ACTIVITY

| Trial | Sporoz No.[1] | Concentration (ug/ml) | | | | Coban[2] | Co:Cmpd |
|---|---|---|---|---|---|---|---|
| | | 0 | 2.5 | 5.0 | 10.0 | 50.0 | | |
| #1 | 39K | 1.0[3] | 1.6 | 1.5 | 1.8 | 2.6 | 3.7 | 1.4[4] |
| #2 | 45K | 1.0 | 1.5 | 3.3 | 3.8 | 12.1 | 10.3 | 0.9 |
| #3 | 68K | 1.0 | NE[5] | NE | 1.8 | 17.9 | 10.4 | 0.6 |

[1] Number of sporozoites added per well
[2] Coban used as a positive control at 5 ug/ml
[3] Anticoccidia scores are determined by dividing the total number of sporozoites observed in the nontreated control well (0 ug/ml) by the number of sporozoites observed in the treated wells. Thus a score of 1.0 is the score of the nontreated controls. The higher the score the more anticoccidial activity.
[4] The Coban to Compound ratio is the comparison of the Coban score to the highest score achieved by the compound. A score of 1 means the compound is equal to coban. A score of less than 1 indicates a compound has more activity.
[5] NE = Not Evaluated

What is claimed is:

1. A pyranoquinone of the formula:

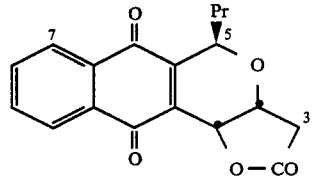

or a physiologically acceptable salt thereof.

2. A method of treating coccidiosis in fowl, said method comprising:
administering a small but coccidiosis treatment effective amount of

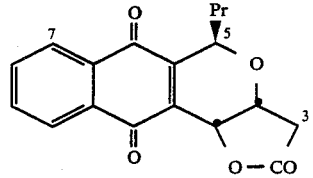

or a physiologically acceptable salt thereof to said fowl.

3. The method of claim 2 wherein administering is by adding pyranoquinone to the feed ration for the fowl.

4. The method of claim 3 wherein the added level is from 50 parts per million of fowl feed ration to 150 parts per million of fowl feed ration.

5. The method of claim 4 wherein the amount of pyranoquinone added to said feed ration is from 90 parts per million to 110 parts per million.

* * * * *